US009913053B2

(12) United States Patent
Jensen et al.

(10) Patent No.: US 9,913,053 B2
(45) Date of Patent: *Mar. 6, 2018

(54) SOUND ENRICHMENT FOR THE RELIEF OF TINNITUS

(75) Inventors: Ole Dyrlund Jensen, Virum (DK); Kim Heegaard Hansen, Roskilde (DK); Luca Del Bo, Milan (IT)

(73) Assignee: GN Hearing A/S, Ballerup (DK)

( * ) Notice: Subject to any disclaimer, the term of this patent is extended or adjusted under 35 U.S.C. 154(b) by 1142 days.

This patent is subject to a terminal disclaimer.

(21) Appl. No.: 12/528,309

(22) PCT Filed: Mar. 7, 2008

(86) PCT No.: PCT/DK2008/000093
§ 371 (c)(1),
(2), (4) Date: Nov. 17, 2010

(87) PCT Pub. No.: WO2008/106974
PCT Pub. Date: Sep. 12, 2008

(65) Prior Publication Data
US 2011/0054241 A1 Mar. 3, 2011

Related U.S. Application Data

(60) Provisional application No. 60/905,670, filed on Mar. 7, 2007.

(30) Foreign Application Priority Data

Mar. 7, 2007 (DK) .................................. 2007 00346

(51) Int. Cl.
*H04R 25/00* (2006.01)
*A61M 21/02* (2006.01)
(Continued)

(52) U.S. Cl.
CPC ............. *H04R 25/75* (2013.01); *A61M 21/02* (2013.01); *G10L 25/84* (2013.01); *H04R 3/04* (2013.01);
(Continued)

(58) Field of Classification Search
CPC ........ H04R 25/00; H04R 25/75; A61N 1/361; A61B 5/128; A61F 11/00; A61M 2021/0027
(Continued)

(56) References Cited

U.S. PATENT DOCUMENTS 4,052,564 A 10/1977 Propst et al.
4,170,764 A 10/1979 Salz et al.
(Continued)

FOREIGN PATENT DOCUMENTS

CN 1813491 A 8/2006
CN 101637420 A 2/2010
(Continued)

OTHER PUBLICATIONS

International Search Report for International Application No. PCT/DK2008/000094.
(Continued)

*Primary Examiner* — Charles A Marmor, II
*Assistant Examiner* — Shannon McBride
(74) *Attorney, Agent, or Firm* — Vista IP Law Group, LLP

(57) ABSTRACT

A sound enrichment system for provision of tinnitus relief, the sound enrichment system includes a noise generator, at least one signal modulator for random or pseudo-random modulation of a noise signal that is obtained using the noise generator, and an output transducer for conversion of the modulated noise signal to an acoustic signal for presentation to a user. A method of providing a noise enriched sound
(Continued)

Figure 1:
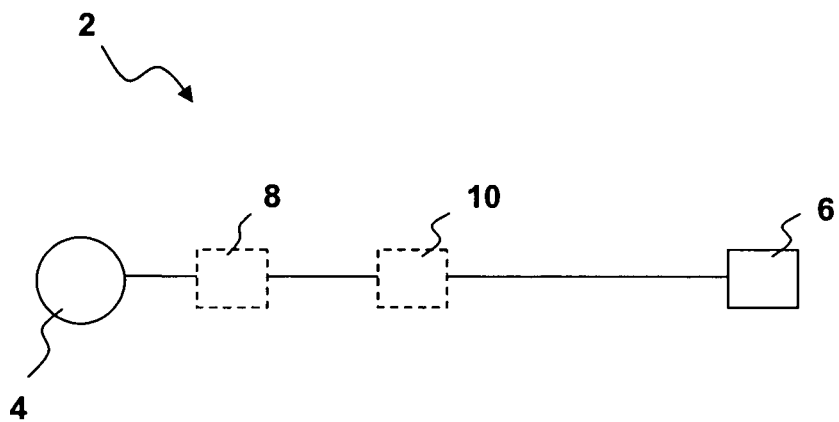

signal for provision of relief of tinnitus includes generating a randomly or pseudo-randomly modulated noise signal, generating an acoustic noise signal using the modulated noise signal, and presenting the acoustic noise signal to a tinnitus suffering person.

67 Claims, 9 Drawing Sheets

(51) Int. Cl.
*G10L 25/84* (2013.01)
*H04R 3/04* (2006.01)
*A61M 21/00* (2006.01)

(52) U.S. Cl.
CPC . *A61M 2021/0027* (2013.01); *A61M 2205/50* (2013.01); *A61M 2210/0662* (2013.01)

(58) Field of Classification Search
USPC ............... 600/25, 28; 381/58–60, 23.1, 72, 381/312–322; 607/55–57; 623/10
See application file for complete search history.

(56) References Cited

U.S. PATENT DOCUMENTS

| | | | |
|---|---|---|---|
| 4,335,710 A * | 6/1982 | Williamson | 600/28 |
| 4,759,070 A * | 7/1988 | Voroba et al. | 381/60 |
| 4,887,299 A | 12/1989 | Cummins et al. | |
| 5,384,853 A | 1/1995 | Kinoshita et al. | |
| 5,403,262 A * | 4/1995 | Gooch | 600/28 |
| 5,521,325 A | 5/1996 | Takeuchi et al. | |
| 5,795,287 A * | 8/1998 | Ball | H04R 25/502 600/25 |
| 6,047,074 A | 4/2000 | Zoels et al. | |
| 6,048,305 A | 4/2000 | Bauman et al. | |
| 6,307,893 B1 | 10/2001 | Bremer et al. | |
| 6,816,599 B2 * | 11/2004 | Thiede | G10H 1/26 381/314 |
| 6,846,284 B2 * | 1/2005 | Choy | 600/28 |
| 6,901,362 B1 | 5/2005 | Jiang et al. | |
| 7,995,770 B1 | 8/2011 | Simon | |
| 7,995,771 B1 * | 8/2011 | Faltys | H04R 25/407 381/313 |
| 8,043,203 B2 | 10/2011 | Park et al. | |
| 8,801,592 B2 * | 8/2014 | Jensen | H04R 25/75 381/312 |
| 2001/0051776 A1 | 12/2001 | Lenhardt | |
| 2002/0090100 A1 | 7/2002 | Thiede et al. | |
| 2002/0191799 A1 * | 12/2002 | Nordqvist et al. | 381/60 |
| 2004/0131200 A1 | 7/2004 | Davis | |
| 2004/0136542 A1 * | 7/2004 | Denda | 381/60 |
| 2004/0183690 A1 | 9/2004 | Nakagawa et al. | |
| 2006/0167335 A1 | 7/2006 | Park et al. | |
| 2006/0227018 A1 | 10/2006 | Ejima | |
| 2006/0233407 A1 | 10/2006 | Steinbuss | |
| 2007/0009126 A1 | 1/2007 | Fischer | |
| 2007/0081680 A1 | 4/2007 | Yen | |
| 2007/0121976 A1 | 5/2007 | Pedersen et al. | |
| 2007/0127755 A1 * | 6/2007 | Bauman | H04R 25/00 381/328 |
| 2007/0133832 A1 * | 6/2007 | DiGiovanni | H04R 25/552 381/320 |
| 2007/0270920 A1 | 11/2007 | Turner | |
| 2008/0080719 A1 | 4/2008 | Ahn et al. | |
| 2008/0170719 A1 | 7/2008 | Shimura et al. | |
| 2009/0028352 A1 * | 1/2009 | Petroff | 381/61 |
| 2009/0030321 A1 | 1/2009 | Baba et al. | |
| 2009/0208030 A1 | 8/2009 | Anderson et al. | |
| 2009/0270673 A1 * | 10/2009 | Abolfathi et al. | 600/25 |
| 2010/0008526 A1 | 1/2010 | de Vries et al. | |
| 2011/0054241 A1 | 3/2011 | Jensen | |
| 2011/0071340 A1 | 3/2011 | Mcguire | |
| 2012/0219169 A1 | 8/2012 | Tong et al. | |
| 2013/0243227 A1 | 9/2013 | Kinsbergen | |

FOREIGN PATENT DOCUMENTS

| | | |
|---|---|---|
| CN | 101641967 A | 2/2010 |
| CN | 101641968 A | 2/2010 |
| CN | 102075842 A | 5/2011 |
| CN | 102462583 A | 5/2012 |
| DE | 4427216 A1 | 2/1996 |
| DE | 29718503 U1 | 4/1999 |
| EP | 0820211 A1 | 1/1998 |
| EP | 1 205 904 A1 | 5/2002 |
| EP | 2 132 957 B1 | 11/2010 |
| EP | 1 658 754 B1 | 10/2011 |
| GB | 2134689 A | 8/1984 |
| GB | 2235349 A | 2/1991 |
| JP | S62-032427 A | 2/1987 |
| JP | H05-023396 A | 2/1993 |
| JP | HEI 06204749 | 7/1994 |
| JP | 10-80000 A | 3/1998 |
| JP | 2004-070267 A | 3/2004 |
| JP | 2004-513725 | 5/2004 |
| JP | 2005-519686 A | 7/2005 |
| JP | 2008-264681 A | 11/2008 |
| JP | 2009-049959 A | 3/2009 |
| JP | 2010-520683 A | 6/2010 |
| JP | 2014-007740 A | 1/2014 |
| WO | 9600051 | 1/1996 |
| WO | 9907302 | 2/1999 |
| WO | 0176321 | 10/2001 |
| WO | 0241296 A1 | 5/2002 |
| WO | WO 03/077511 A1 | 9/2003 |
| WO | 2004098690 | 11/2004 |
| WO | WO 2004098690 A1 * | 11/2004 ............ A61M 21/00 |
| WO | 2006030373 | 3/2006 |
| WO | WO 2008/106974 A2 | 9/2008 |
| WO | WO 2008/106975 A2 | 9/2008 |
| WO | WO 2008/134345 A1 | 11/2008 |

OTHER PUBLICATIONS

Written Opinion of the International Searching Authority for International Application No. PCT/DK2008/000094.
Pawel J. Jastreboff, Tinnitus Habituation Therapy (THT) and Tinnitus Retraining Theraphy (TRT). In Tyler RS, ed. Handbook of Tinnitus, San Diego: Singular Publishing, 2000, pp. 357-376.
Luca Del Bo et al, "Using Open-Ear Hearing Aids in Tinnitus Theraphy" BTE and Open Hearing Aid Fittings: Hearing Research, Hearing Review, Aug. 2006.
International Search Report for Application No. PCT/DK2008/000093.
Written Opinion of the International Searching Authority for Application No. PCT/DK2008/000093.
Japanese Notice of Reason for Refusal and Written Directive dated Aug. 28, 2012, for Japanese Patent Application No. 2009-552065.
English Translation of Japanese Notice of Reason for Refusal and Written Directive dated Aug. 28, 2012, for Japanese Patent Application No. 2009-552065.
Danish Examination Report dated Oct. 11, 2007, for Danish Patent Application No. PA 2007-00346.
Chinese Office Action dated Apr. 30, 2014 for related Chinese Patent App. No. 200880007383.8, 19 pages.
Extended European Search Report dated Apr. 21, 2016 for related EP Patent Application No. 15199421.7, 10 pages.
Japanese Decision of Rejection dated Apr. 5, 2016 for related JP Patent Application No. 2014-203803, 7 pages.
Extended European Search Report dated Nov. 28, 2012 for related EP Patent Application No. 12173634.2.
First Technical Examination and Search Report dated Dec. 21, 2012, for related DK Patent Application No. PA 2012 70372.
Second Technical Examination, Intention to Grant dated Jun. 26, 2013 for related DK Patent Application No. PA 2012 70372.
Notification of Reason for Rejection dated Jul. 28, 2015, for corresponding Japanese Patent Application No. 2014-19816, 7 pages.
Notification of Reason for Rejection dated Sep. 24, 2015, for corresponding Japanese Patent Application No. 2014-203803, 11 pages.

(56) References Cited

OTHER PUBLICATIONS

First Chinese Office Action dated May 26, 2016 for related Chinese Patent Application No. 2013-10674848.8.
Communication pursuant to Article 94(3) EPC dated Aug. 28, 2017 for related European Patent Application No. 15199421.7, 7 pages.
Anonymous: "Natural Sounds"—Wikipedia, May 19, 2012, 4 pages.

* cited by examiner

SOUND ENRICHMENT FOR THE RELIEF OF TINNITUS

RELATED APPLICATION DATA

This application is the national stage of International Application No. PCT/DK2008/000093, filed on Mar. 7, 2008, which claims priority to and the benefit of Denmark Patent Application No. PA 2007 00346, filed on Mar. 7, 2007, and U.S. Provisional Patent Application No. 60/905,670, filed on Mar. 7, 2007, the entire disclosure of all of which is expressly incorporated by reference herein.

FIELD

The present application relates to a new sound enrichment system for the provision of relief of tinnitus. The present application further relates to a software program implementing a part of the sound enrichment system. Additionally, the present application further relates to a method of providing an enriched sound signal for the provision of relief of tinnitus.

BACKGROUND

Tinnitus is the perception of sound in the human ear in the absence of corresponding external sound(s). Tinnitus is considered a phantom sound, which arises in the auditory system. For example, a ringing, buzzing, whistling, or roaring sound may be perceived as tinnitus. Tinnitus can be continuous or intermittent, and in either case can be very disturbing, and can significantly decrease the quality of life for one who has such an affliction.

Tinnitus is not itself a disease but an unwelcome symptom resulting from a range of underlying causes, including psychological factors such as stress, disease (infections, Menieres Disease, oto-sclerosis, etc.), foreign objects or wax in the ear and injury from loud noises. Tinnitus is also a side-effect of some medications, and may also result from an abnormal level of anxiety and depression.

The perceived tinnitus sound may range from a quiet background sound to a signal loud enough to drown out all outside sounds. The term 'tinnitus' usually refers to more severe cases. A 1953 study of 80 tinnitus-free university students placed in a soundproofed room found that 93% reported hearing a buzzing, pulsing or whistling sound. However, it must not be assumed that this condition is normal—cohort studies have demonstrated that damage to hearing from unnatural levels of noise exposure is very widespread.

Tinnitus can, to date, not be surgically corrected and since, to date, there are no approved effective drug treatments, so-called tinnitus maskers have become known. These are small, battery-driven devices which are worn like a hearing aid behind or in the ear and which, by means of artificial sounds which are emitted, for example, via a hearing aid speaker into the auditory canal, to thereby psycho acoustically mask the tinnitus and thus reduce the tinnitus perception.

The artificial sounds produced by the maskers are often narrow-band noise. The spectral position and the loudness level of the noise can often be adjusted via for example a programming device to enable adaptation to the individual tinnitus situation as optimally as possible. In addition, so-called retraining methods have been developed, for example tinnitus retraining therapy (Jastreboff P J. Tinnitus habituation therapy (THI) and tinnitus retraining therapy (TRT). In: Tyler R S, ed. *Handbook of Tinnitus*. San Diego: Singular Publishing; 2000:357-376) in which, by combination of a mental training program and presentation of broad-band sound (noise) near the auditory threshold, the perceptibility of the tinnitus in quiet conditions is likewise supposed to be largely suppressed. These devices are also called "noisers" or "sound enrichment devices". Such devices or methods are for example known from DE 29718 503, GB 2 134 689, US 2001/0051776, US 2004/0131200 and U.S. Pat. No. 5,403,262.

Another system is known from WO 2004/098690, wherein spatial filtering is used in a binaural hearing aid system, i.e. a hearing aid system containing two hearing aids, wherein the input signals to the two devices are manipulated in such a way that the perceived direction of origin of the input signal is altered in a number of different ways. It is mentioned that the spatial filtering may be obtained by changing the spectral properties of the incoming sound signal along with a manipulation of the phase and signal level of the incoming sound signal. For example, the signal level is manipulated in dependence of the input signal level in resemblance with an automatic gain control circuit. It is alleged that such a system may provide relief for, and even treatment of, tinnitus.

From U.S. Pat. No. 6,047,074 is known a hearing aid comprising a signal generator for the provision of a noise signal employable in tinnitus therapy. The disclosed hearing aid also includes a signal analysis stage by which the input signal of the hearing aid may be analyzed. The input signal spectrum can then be analyzed in order to find out if an adequately high signal level is present in the frequency range that is needed for tinnitus therapy. If this is the case, then the signal generator is not activated. If however, the input signal level is low, then the signal generator is activated. The decision to apply the tinnitus therapy signal is thus merely based on the input signal of the hearing aid.

Although present day tinnitus maskers to a certain extent may provide immediate relief of tinnitus, the masking sound produced by them is very monotonous and therefore unpleasant for the user of such a masker. Investigations show that tinnitus is a condition that requires long term treatment in order to achieve good results. However, the listening to highly monotonic masking sounds during such a long time may be a severe annoyance to a user of such a masker.

For many people, the known maskers will not provide any long term relief of tinnitus. Recent research conducted by Del Bo, Ambrosetti, Bettinelli, Domenichetti, Fagnani, and Scotti "Using Open-Ear Hearing Aids in Tinnitus Therapy", Hearing Review, August 2006, has indicated that better long term prospectives for tinnitus relief may be achieved if so-called habituation of tinnitus is induced in a tinnitus sufferer by using sound enrichment by sound from the ambient environment. The rationale behind habituation relies on two fundamental aspects of brain functioning: Habituation of the reaction of the limbic and sympathetic system, and habituation of sound perception allowing a person to ignore the presence of tinnitus. While tinnitus maskers emit sounds that either partly or completely cover the perceived sound of tinnitus, Del Bo, Ambrosetti, Bettinelli, Domenichetti, Fagnani, and Scotti, suggest the use of environmental sounds amplified by a hearing aid or by application of artificial sounds, such as band limited noise.

However since, traditional sound enrichment often has to be used for many months in order to achieve the habituation of a person's perception of tinnitus, the monotony of the used sound signal may be annoying and uncomfortable for some users to listen to.

SUMMARY

It is thus an object to provide an alternative sound enrichment system for the provision of relief of tinnitus that would be comfortable for many users to listen to.

It is a further object to provide an alternative method of providing a noise enriched sound signal, for the provision of relief of tinnitus that would be comfortable for many users to listen to.

It is an even further object to provide a software program product stored on a machine readable data storage device which when executed on a processing device at least in part executes the method of providing a noise enriched sound signal.

According to some embodiments, the above-mentioned and other objects are fulfilled by a sound enrichment system for the provision of relief of tinnitus, the sound enrichment system comprising: A noise generator for the provision of a noise signal, an output transducer that is configured to convert the noise signal into an acoustic signal that during use of the sound enrichment system is presented to a user, wherein the sound enrichment system further comprises at least one signal modulator that is configured to randomly or pseudo-randomly modulate the noise signal. Thus, conversion of the noise signal preferably comprises conversion of a modulated noise signal. In an embodiment, only the noise signal modulated by the at least one signal modulator is converted into an acoustic signal.

By the provision of a sound enrichment system with a signal modulator that is configured to randomly or pseudo-randomly modulate the generated noise signal, the monotony of the noise signal is broken, whereby it is achieved that the (modulated) noise signal would be comfortable for many users to listen to, even for longer periods of time.

The modulator and the noise generator may comprise one single unit whereby it would be possible to generate a randomly or pseudo-randomly modulated noise signal. Further, the noise generator and the modulator may in one embodiment comprise two separate units that may be operatively connected to each other.

In a preferred embodiment, the noise generator is a noise generator that generates a white noise signal. Here, white noise is a random signal (or process) with a substantially flat power spectral density within the operating frequency range of the white noise generator. In other words, the signal's power spectral density has substantially equal power in any frequency band, at any centre frequency, having a given bandwidth. White noise is considered analogous to white light which contains all frequencies.

The term white noise is also commonly applied to a noise signal which has zero autocorrelation. The signal is then "white" in the frequency domain. In one embodiment, the noise generator generates a white noise signal in the frequency domain. Being uncorrelated in time does not, however, restrict the values a signal can take. Any distribution of values is possible (although it must have zero DC component).

For example, a binary signal which can only take on the values 1 or 0 will be white if the sequence of zeros and ones is statistically uncorrelated. Noise having a continuous amplitude distribution, such as a normal distribution, can also be white. It is often incorrectly assumed that Gaussian noise (i.e. noise with a Gaussian amplitude distribution) is necessarily white noise. However, neither property implies the other. The term Gaussian refers to the way signal values are distributed, while the term 'white' refers to correlations at two distinct times, which are independent of the noise amplitude distribution. In another embodiment, the noise generator generates Gaussian white noise or Poissonian white noise. Hereby is achieved a noise generator that is configured to generate white noise that is a good approximation of many real-world situations and which may be generated by use of standard mathematical models. A further advantage of Gaussian white noise is that its values are independent.

For certain users of the inventive sound enrichment system it may be advantageous to use frequency weighing of noise (commonly referred to as coloration). Thus, in an alternative embodiment, the noise generator generates a noise signal that has another colour than white, for example pink, blue or brown.

The random or pseudo-random modulations of the noise signal may in an embodiment comprise randomly or pseudo-randomly choosing a modulation value from an event space of modulation values. In an embodiment, the event space of modulation values is a predetermined event space from which the modulation value is chosen.

The random or pseudo-random modulations of the noise signal may, alternatively or additionally, comprise randomly or pseudo-randomly choosing a modulation period from an event space of modulation periods. In an embodiment, the event space of modulation periods is a predetermined event space from which the modulation period is chosen. The modulation period may for example be the time-span between modulation events, such as the time span between two chosen modulation values. Preferably, the modulation period is the time-span between two successively chosen modulation values.

In an embodiment, the modulator may be configured to modulate the noise signal according to a method comprising the steps of: Randomly or pseudo-randomly choosing a modulation value from an event space of modulation values, and randomly or pseudo-randomly choosing a modulation period from an event space of modulation periods.

In yet an embodiment, the modulation value or the modulation period is fixed to a certain value.

An aspect of some of the embodiments described herein relates to a noise generator for the generation of an audio signal (which audio signal may be converted to a sound signal in an output transducer, such as a speaker, loudspeaker or a receiver), wherein the noise generator comprises a signal modulator which is configured to modulate the audio signal according to a method that comprises: Randomly or pseudo-randomly choosing a modulation value from an event space of modulation values, and randomly or pseudo-randomly choosing a modulation period from an event space of modulation periods.

In order to provide a less monotonous noise signal, the sound enrichment system according to another preferred embodiment comprises at least one signal modulator for modulation of the amplitude of the noise signal that is generated by the noise generator.

In order to provide an even less monotonic noise signal, the sound enrichment system according to another preferred embodiment, comprises at least one signal modulator for modulation of the amplitude of the noise signal at a slower rate than the rate of the amplitude variations that are inherent in the noise signal. Furthermore, such slower modulations would, for many users, be more comfortable to listen to than fast modulations.

In one embodiment, the rate at which the amplitude modulations is performed, may be somewhere between 0.5 seconds and 20 seconds (i.e. the event space of modulation periods is in this embodiment the interval [0.5 seconds-20 seconds]), preferably between 1 second and 15 seconds, and yet even more preferably between 2 seconds and 10 seconds. The intervals may in another embodiment refer to the period of modulation.

Alternatively, the rate at which the amplitude modulations are performed may be a certain suitably chosen order of magnitude slower than the rate of the amplitude variations that are inherent in the noise signal. For example the rate at which the amplitude modulations is performed, may be a factor of 10, 20, 30, 40, 50, 60, 70, 80, 90, 100, 200, 300 slower than the rate of the amplitude variations that are inherent in the noise signal.

The size (or value) of the amplitude modulations of the noise signal may in a preferred embodiment be somewhere between 0 dB and 20 dB (i.e. the event space of modulation values is in this embodiment the interval [0 dB-20 dB]), preferably between 0 dB and 15 dB, even more preferably between 0 dB and 10 dB, and yet even more preferably between 0 dB and 7 dB. For example the size (or value) of the amplitude modulations of the noise signal may be chosen (possible randomly or pseudo-randomly chosen) to be 0 dB, or 1 dB, or 2 dB, or 3 dB, or 4 dB, or 5 dB, or 6 dB, or 7 dB. Note that modulation values may as well range between 0 dB and downwards instead of upwards as indicated above. Likewise, modulation values may as well comprise both positive and negative values measured in dB.

In an alternative preferred embodiment of the sound enrichment system, the at least one modulator is configured to modulate selected spectral characteristics of the noise signal.

Hereby an alternative way is achieved of providing a non-monotonous noise signal that would be more comfortable for many users to listen to.

Preferably the modulation of selected spectral characteristics of the noise signal may be performed at a slower rate than the rate of variations of the selected spectral characteristics that are inherent in the noise signal, to thereby provide a modulated noise signal that is even more desirable and comfortable for many users to listen to.

In a preferred embodiment, the sound enrichment system comprises a noise generator and at least one signal modulator (possibly provided as a single unit) that may be configured to generate a modulated noise signal, wherein both the amplitude and selected spectral characteristics of the noise signal may be modulated, for example substantially simultaneously.

In a preferred embodiment, the sound enrichment system further comprises a spectral shaping filter for at least in part filtering the noise signal, and wherein the at least one signal modulator that is configured to modulate selected spectral characteristics of the noise signal by a variation of the frequency response of the spectral shaping filter. Hereby an easily configurable implementation of the modulation of the selected spectral characteristics of the generated noise signal, in which standard filter theory may be utilized, is provided.

The modulation of the frequency response of the spectral shaping filter may in one embodiment comprise a modulation of at least one of the filter parameters chosen from the group: Stop-band frequency, slope/octave, number and/or placement of the poles and/or zeroes of the filter transfer function, or any combination of the filter parameters. Thus, the modulation value comprises in this case one or more values identifying the relevant filter parameter(s).

In one embodiment, the spectral shaping filter is a single band pass filter. The frequency range of the band pass filter may preferably be in the range of 0.2 kHz to 15 kHz, more preferably in the range of 0.4 kHz to 10 kHz, or in the range of 0.5 kHz to 7 kHz, or yet more preferably in the range of 0.7 kHz to 7 kHz, for example in the range of 1 kHz to 6 kHz.

The spectral shaping filter may comprise a set of suitably chosen filters, for example a set of bandpass filters, whereby the noise signal may be filtered and further, the modulation of the amplitude or the spectral characteristics of the generated noise signal may be performed in each band. Further, the modulation of the amplitude or the spectral characteristics of the generated noise signal may be performed in only some of the bands. Further, in one embodiment, both the modulation of the amplitude and the spectral characteristics of the generated noise signal are performed in each band. Further, the modulation of the amplitude and the spectral characteristics of the generated noise signal may be performed in only some of the bands. The frequency range of the set of bandpass filters may cover any of the frequency ranges mentioned above.

In a preferred embodiment, the spectral shaping filter comprises a low-pass filter and a high-pass filter. The cut-off frequency of the low-pass filter may for example range from 0.5 kHz to 3 kHz, and the cut-off frequency of the high-pass may for example range from 2 kHz to 6 kHz.

In order to achieve computational simplicity, the spectral shaping filter in one embodiment is a Butterworth filter, for example a third order IIR Butterworth filter. However 2'nd order filtering may be used instead in order to reduce computational requirements. Alternatively, the spectral shaping filter may in one embodiment comprise a Chebyshev filter or a FIR filter.

One embodiment of the sound enrichment system further comprises an environment classifier that is configured to at least in part classify the ambient sound environment of the sound enrichment system, and wherein the at least one modulator may be configured to modulate the noise signal in dependence of a classification of the ambient sound environment of the sound enrichment system. Hereby, a sound enrichment system is provided that for example may be configured to provide a modulated acoustical noise signal that has a lower average signal pressure level in those situations wherein noise is present in the ambient sound environment, since in those situations the provision of additional noise by the noise enrichment system may not be needed. Also the modulation may be performed in dependence of what kind of noise is already present in the ambient sound environment. Another advantage is that the modulation of the generated noise signal may be dependent on whether speech is present in the ambient sound environment. For example the modulation of the generated noise signal may be performed in such a way that the provided acoustical noise signal may be damped to such an extent that it does not interfere with a user's perception of the speech. This may be of importance to many users of the inventive sound enrichment system, because speech is very often a sound that is desirable for a user of the sound enrichment system to hear. This may be especially important for those tinnitus sufferers which in addition to tinnitus also suffer from a reduced ability to understand speech in noise, because an addition of an acoustical noise signal generated by the sound enrichment system may adversely affect the tinnitus sufferer's intelligibility of speech.

In a preferred embodiment, the environment classifier comprises a speech detector. In one preferred embodiment, the environment classifier is a speech detector. A speech detector may for example be configured to detect presence of speech by analyzing the envelope of an input signal. In an embodiment, the environment classifier is configured to classify the ambient environment according to a number of distinguishable sound classes. These sound classes can for example comprise: clean speech (or substantially clean speech), and/or speech in noise or music and/or noise. The noise sound class can for example be subdivided into a number of different types of noise classes, for example: Traffic noise, wind noise, restaurant noise, or "cocktail party" noise. Cocktail party noise is usually the sound field generated when many (at least two) people are talking substantially simultaneously in the same room or environment. A sound class can be any combination of the above mentioned sound classes, i.e. for example speech in traffic noise, music in cocktail party noise, etc. The presence of a sound class (which may be a combination of individual sound classes) as determined by the environment classifier will preferably influence the specific adjustment (or modulation(s)) of the generated noise signal, so that an optimal adjustment of the noise signal used for relief of tinnitus may be achieved in each type of sound environment. Preferably the adjustment of the noise signal is done in such a way as to provide maximum speech intelligibility and at the same time provide maximum relief of tinnitus. In an embodiment, a user of the sound enrichment system may set whether the sound enrichment system shall provide maximum speech intelligibility or maximum relief of tinnitus. In a preferred embodiment, a user may adjust the degree of provision of relief of tinnitus in relation of the degree of speech intelligibility. A user may adjust or set the relation for instance using a physical switch, like for example a toggle wheel or another form of mechanical or electrical (or optionally magnetic, magneto-resistive or giant magneto-resistive) contact. Alternatively or in combination, such a switch may be software controlled. Such a software controlled switch may for example be enabled or disabled by a user, by a suitable choice of program(s).

In order to account for nonlinearities in the output transducer, which preferably is a receiver, the sound enrichment system in one embodiment further comprises a transducer response equalization filter that may be provided in the signal path of the noise signal between the noise generator and the output transducer.

In a preferred embodiment of the sound enrichment system, the modulations of the spectral characteristics of the noise signal enable the frequency range of the noise signal to be adjusted, for example by adjusting suitably chosen stopband and/or passband frequencies of the spectral shaping filter. For example, the frequency range may even be individually adjustable (for example by a fitter), possibly to exclude the frequency range of the perceived tinnitus of a tinnitus sufferer. Alternatively, the frequency range of the noise signal may be adjusted to a certain suitably chosen default range, whereby the desired habituation may be achieved. In an embodiment, modulation of selected spectral characteristics of the noise signal comprises a frequency shift of at least one or more parts of the noise signal generated by the noise generator. For instance, a narrow noise signal may be frequency shifted such that the resulting modulated noise signal cover a desired frequency range.

In one embodiment of the sound enrichment system, the frequency range of the noise signal is individually adapted to comprise frequencies substantially lower than the frequency of the perceived tinnitus. This way habituation of the perceived tinnitus may be achieved, since many users will subconsciously focus on the more pleasant randomly or pseudo-randomly generated low frequency noise signal, and in the course of time adapt their brains to ignore the perceived tinnitus altogether. As such sound enrichment is significantly different from masking, since masking is achieved by drowning the perceived tinnitus by a competing signal that is sensed by the sensi-neural cells of a user's ear. Sound enrichment may bring about an effect on a much higher level in a user's auditory system, which will enable him or her to at least in part ignore the perceived tinnitus.

Since many persons that suffer from tinnitus also suffer from a hearing loss, the sound enrichment system according to a preferred embodiment forms part of a hearing aid. Hereby, the hearing aid may be able to account for both the hearing loss of a user as well as providing relief for a user's perceived tinnitus. In this embodiment, the output transducer of the hearing aid is the same as the output transducer of the sound enrichment system.

A hearing aid may comprise a sound enrichment system according to some embodiments. In a preferred embodiment, the hearing aid comprises: A microphone for the provision of an input signal, a signal processor for processing of the input signal into an output signal, including (preferably frequency dependent) amplification of the input signal for compensation of a hearing loss of a wearer of the hearing aid, and a receiver for the conversion of the output signal into an output sound signal to be presented to the user of the hearing aid, wherein the hearing aid further comprises a noise generator for the provision of a noise signal having a certain average signal level and means for adding the noise signal to the output signal of the signal processor. Further, the hearing aid may comprise at least one signal modulator for random or pseudo-random modulation of the noise signal and means for adding the modulated noise signal to the output signal of the signal processor.

The hearing aid may be a behind-the-ear (BTE), in-the-ear (ITE), completely-in-the-canal (CIC), receiver-in-the-ear (RIE) or otherwise mounted hearing aid.

In one embodiment, the hearing aid further comprises a portable personal device that may be operatively connected to the hearing aid processor by for example a wireless or wired link, wherein the portable personal device comprises a noise generator for the provision of a noise signal having a certain average signal level, and wherein the hearing aid signal processor is configured to perform the modulation of the noise signal. Hereby, processing power and memory required for the generation of the noise signal is removed from the hearing aid, which usually has very limited processing power and memory capabilities.

The portable personal device is preferably of such a size and weight that it may easily be configured to be body worn. In a preferred embodiment, the portable personal device is any one of the following: A mobile phone, a PDA, a special purpose portable computing device. The link between the portable personal device and the hearing aid may for example be provided by an electrical wire or some suitable chosen wireless technology, such as Blue Tooth or some other special purpose wireless technology.

Scientific investigations conducted by Del Bo, Ambrosetti, Bettinelli, Domenichetti, Fagnani, Scotti, reported in "Using Open-Ear Hearing Aids in Tinnitus Therapy", Hearing Review, August 2006, show that particularly good results, within a much shorter period of time than is traditionally used, may be obtained if so-called open fitting hearing aids are used in combination with sound enrichment. Thus, in a preferred embodiment, the hearing aid (comprising the inventive sound enrichment system) is configured for being openly fitted to the ear of a user. Such an openly fitted hearing aid may for example be a Resound Air hearing aid or any equivalent hearing aid. Furthermore it may be a Resound Air type of hearing aid, wherein the receiver is configured for being situated in the ear canal of a user. The scientific investigations regarding openly fitted hearing aids used in combination with sound enrichment is further supported by theoretical arguments, since for example persons with tinnitus very often suffer from mild to moderate hearing losses typically at frequencies higher than 1.5 kHz-2 kHz and with limited associated hearing handicap. The so-called pitch of the tinnitus is often found in the frequency range of 3 kHz-8 kHz.

Furthermore, noise enrichment having a level less than 10-15 dB above the audiometric threshold is often enough in order to provide relief for tinnitus. Because openly fitted hearing aids do not occlude the ear canal significantly, and therefore do not induce any major sound attenuation, good amplification within the 2 kHz-6 kHz range can be achieved, supported by effective feedback suppression systems. Thus, these openly fitted hearing aids provide exceptional characteristics for sound enrichment.

The hearing aid may comprise a volume control that is configured to be switched between controlling the level of the noise signal and the hearing aid gain. Hereby is achieved that the volume control of the hearing aid may be used to control the overall level of the noise signal used for the relief of tinnitus and to control the gain of the hearing aid, whereby two separate controls for those two operations is avoided and therefore maximum exploitation of the limited space in a hearing aid is achieved.

The switching between controlling the hearing aid gain and the level of the noise signal may be performed manually. Alternatively or additionally, the switching may be performed in dependence of a classification of the ambient sound environment. By switching manually, it is achieved that the user may actively choose between using the volume control to control the hearing aid gain or the level of the noise signal. Furthermore, since the switching may be performed in dependence of a classification of the ambient sound environment, it may for instance be achieved that the volume control is used to control the hearing aid gain when the level of the noise signal is low (or the sound enrichment system is inactive), and, similarly, that the volume control for instance may be used to control the level of the noise signal when the level of the noise signal is high (or simply when the sound enrichment system is active).

In an embodiment, the volume control is automatically switched to control the level of the noise signal when the sound enrichment system is active, while the hearing aid gain at the same time is controlled by an automatic gain control of the hearing aid. Such an automatic gain control may be any kind of automatic gain control known in the art.

In an embodiment, the sound enrichment system and the volume control of the hearing aid may be operatively linked to each other in such a way, that when the sound enrichment system is activated, automatically in dependence of a classification of the ambient sound environment or manually by the user, e.g. by choosing or switching to a suitable program, the volume control is automatically switched to a mode wherein it may be used to control the level of the noise signal.

Another aspect of some of the embodiments described herein relates to a binaural hearing aid system comprising a first and a second hearing aid (two hearing aids), wherein the first hearing aid and/or the second hearing aid comprises a sound enrichment system. Preferably, both the first and the second hearing aid in the binaural hearing aid system comprises a sound enrichment system.

The two hearing aids of the binaural hearing aid system are in an embodiment operatively connected to each other, and some or all potential modulations of the amplitude and/or some or all potential modulations of selected spectral characteristics of the noise signal may furthermore be performed in an coordinated manner between the two hearing aids. In an embodiment, one of the two hearing aids is operatively connected to the other and some or all potential modulations are coordinated by the one hearing aid. The modulations can for example comprise amplitude modulations or modulations of band pass filtering in the two hearing aids. In an embodiment, the modulations may be coordinated in an asynchronous manner between the two hearing aids, the modulations may for instance be slightly phase shifted relative to each other. Slightly asynchronous relations between the amplitude envelope and frequency band pass filtering between the two hearing aids may make it sound much like listening to breaking waves, as if the user of the binaural hearing aid system is standing on a beach and listening to the waves. Hereby, an even more comfortable noise signal for tinnitus relief is provided for.

The noise generator and/or the signal modulator are in a preferred embodiment implemented in a software program stored on a machine readable data storage device which when executed on a processing device is configured to generate the modulated noise signal. The processing device is in one embodiment a signal processor in a hearing aid; preferably it may be a digital signal processor. Furthermore, the spectral shaping filter and/or the signal level adjuster and/or the receiver response equalization filter may be implemented in a software program stored on a machine readable data storage device as referred to above. Hereby, all parts of the sound enrichment system except the output transducer may be implemented in software. Thus, in those embodiments of the sound enrichment system, wherein the sound enrichment system forms part of a hearing aid, and the output transducer of the sound enrichment system is the receiver of the hearing aid, the generation of a (randomly or pseudo-randomly) modulated noise signal is implemented in a software program that may be a standard program that may be enabled in a signal processor of the hearing aid. This enables the use of sound enrichment as an add-on feature that may be used in a hearing aid, especially an add-on feature of the general software package of a hearing aid.

A further aspect of the some of the embodiments described herein relates to a method of providing a noise enriched sound signal for the provision of relief of tinnitus, the method comprising the steps of (a) generating a randomly or pseudo-randomly modulated noise signal, (b) generating an acoustic noise signal from the modulated noise signal, wherein the acoustic noise signal during use is presented to a tinnitus suffering person.

In one embodiment of the inventive method, the step of generating the modulated noise signal comprises amplitude modulation of the generated noise signal.

The amplitude modulation of the noise signal may be performed at a slower rate than the average rate of the amplitude variations in the noise signal.

The step of generating the modulated noise signal may comprise modulation of selected spectral characteristics of the noise signal.

The modulation of selected spectral characteristics of the noise signal may be performed at a slower rate than the rate (preferably average rate) of the selected spectral variations in the noise signal.

The modulation of selected spectral characteristics of the noise signal may be provided by filtering the noise signal through at least one spectral shaping filter and modulating the frequency characteristics of the spectral shaping filter.

The modulation of the frequency characteristics of the spectral shaping filter may comprise a modulation of at least one of the filter parameters chosen from the group: stop-band frequency, slope/octave, number and/or placement of the poles and/or zeroes of the filter transfer function for the spectral shaping filter.

One further aspect of some of the embodiments described herein relates to software program product stored on a machine readable data storage device which when executed on a processing device executes at least one of the steps of the method as described above.

In accordance with some embodiments, a sound enrichment system for provision of tinnitus relief, the sound enrichment system includes a noise generator, at least one signal modulator for random or pseudo-random modulation of a noise signal that is obtained using the noise generator, and an output transducer for conversion of the modulated noise signal to an acoustic signal for presentation to a user.

In accordance with other embodiments, a method of providing a noise enriched sound signal for provision of relief of tinnitus includes generating a randomly or pseudo-randomly modulated noise signal, generating an acoustic noise signal using the modulated noise signal, and presenting the acoustic noise signal to a tinnitus suffering person.

A further understanding of the nature and advantages of the embodiments may be realized by reference to the remaining portions of the specification and the drawings.

DESCRIPTION OF THE DRAWING FIGURES

Figure 2:
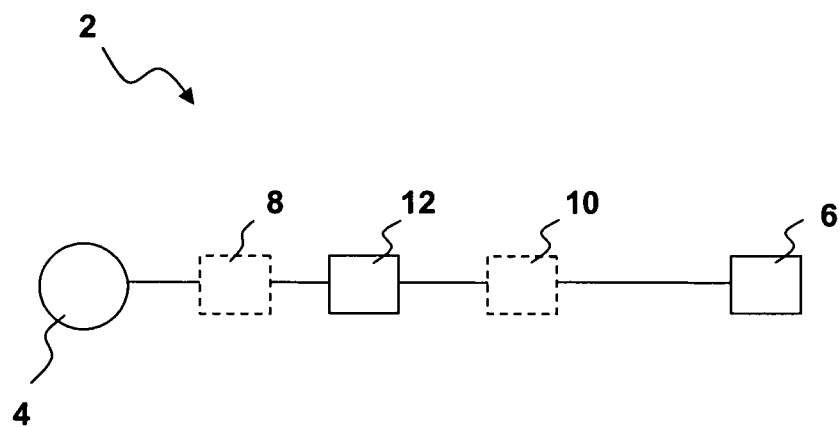
Figure 3:
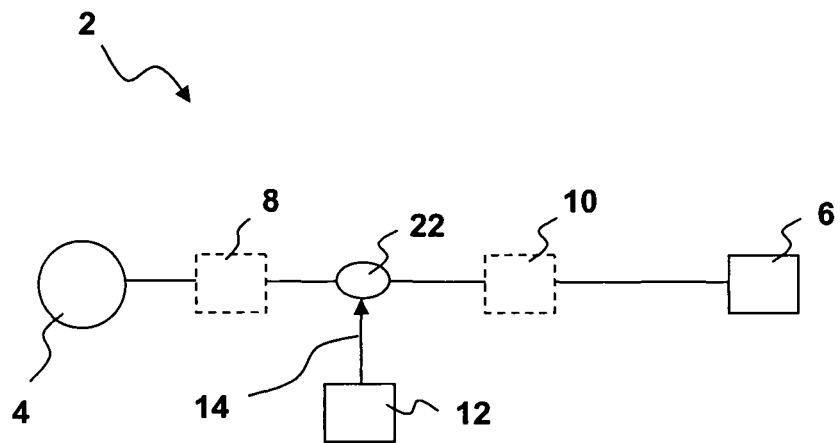
Figure 4:
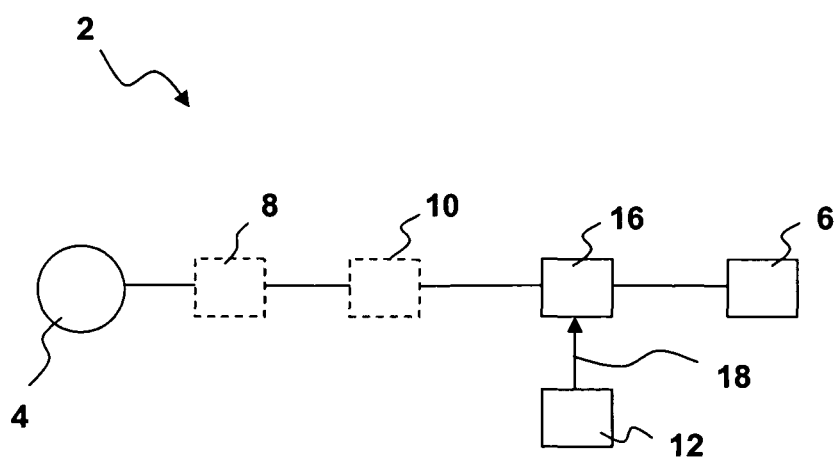
Figure 5:
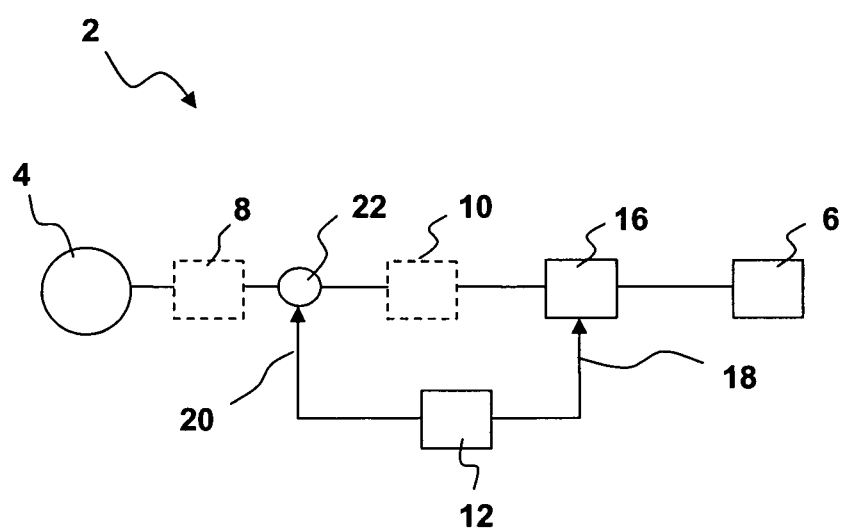
Figure 6:
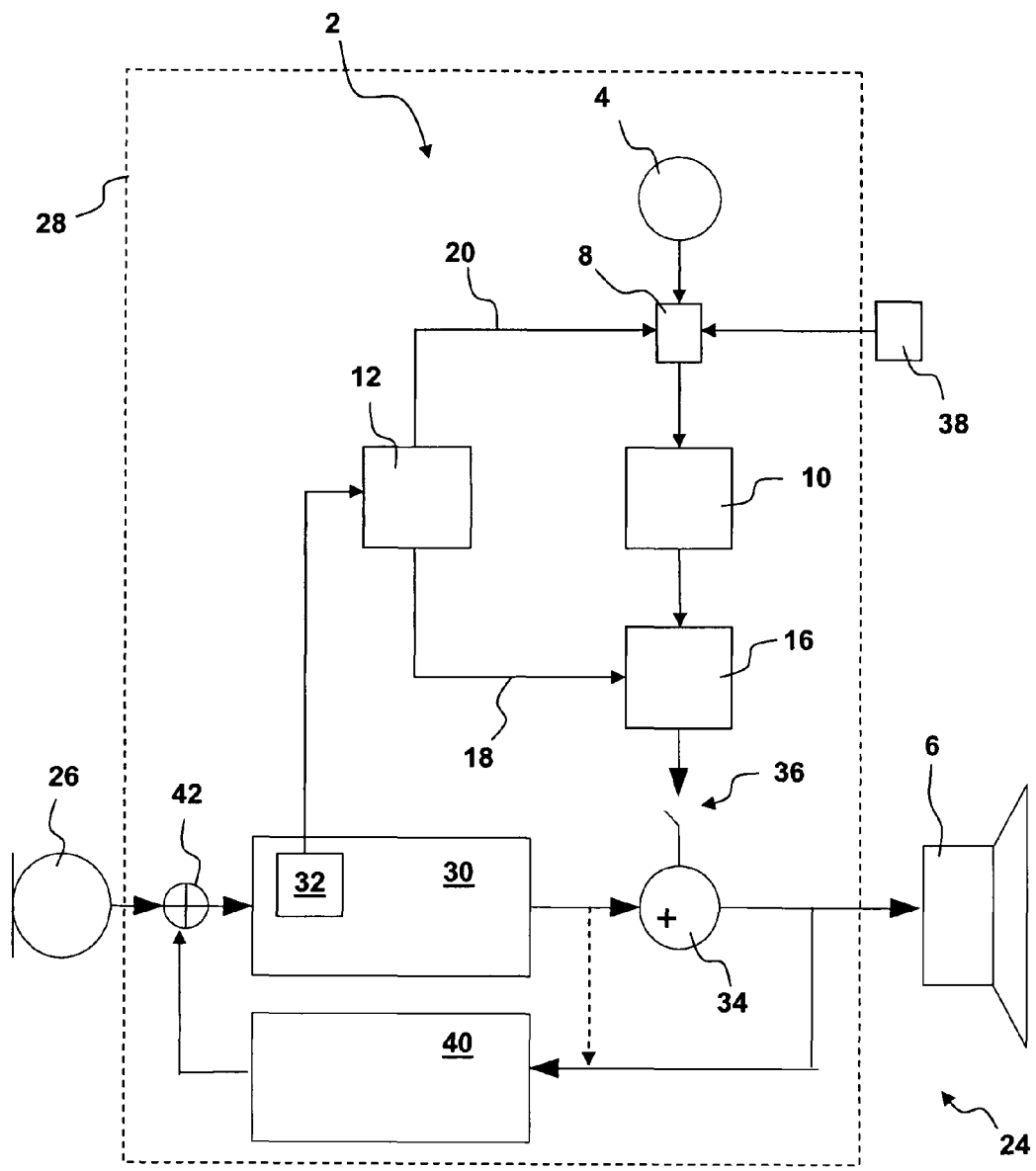
Figure 7:
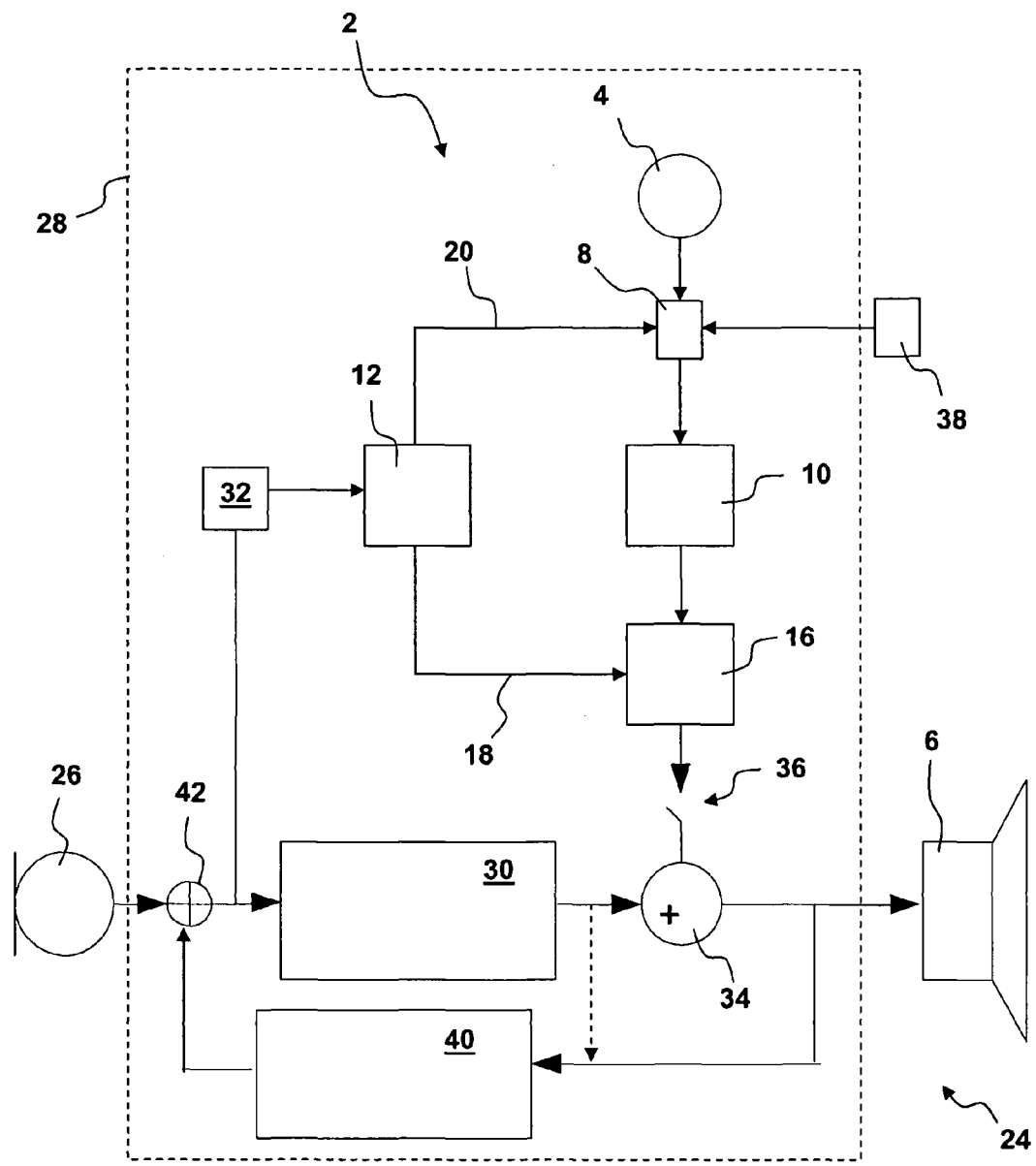
Figure 8:
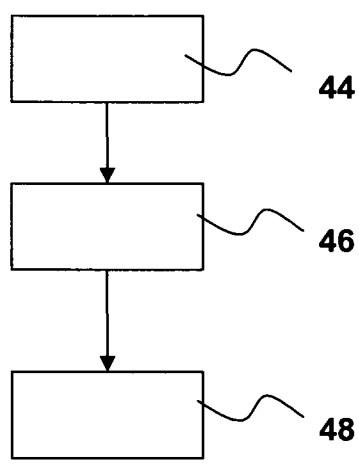
Figure 9:
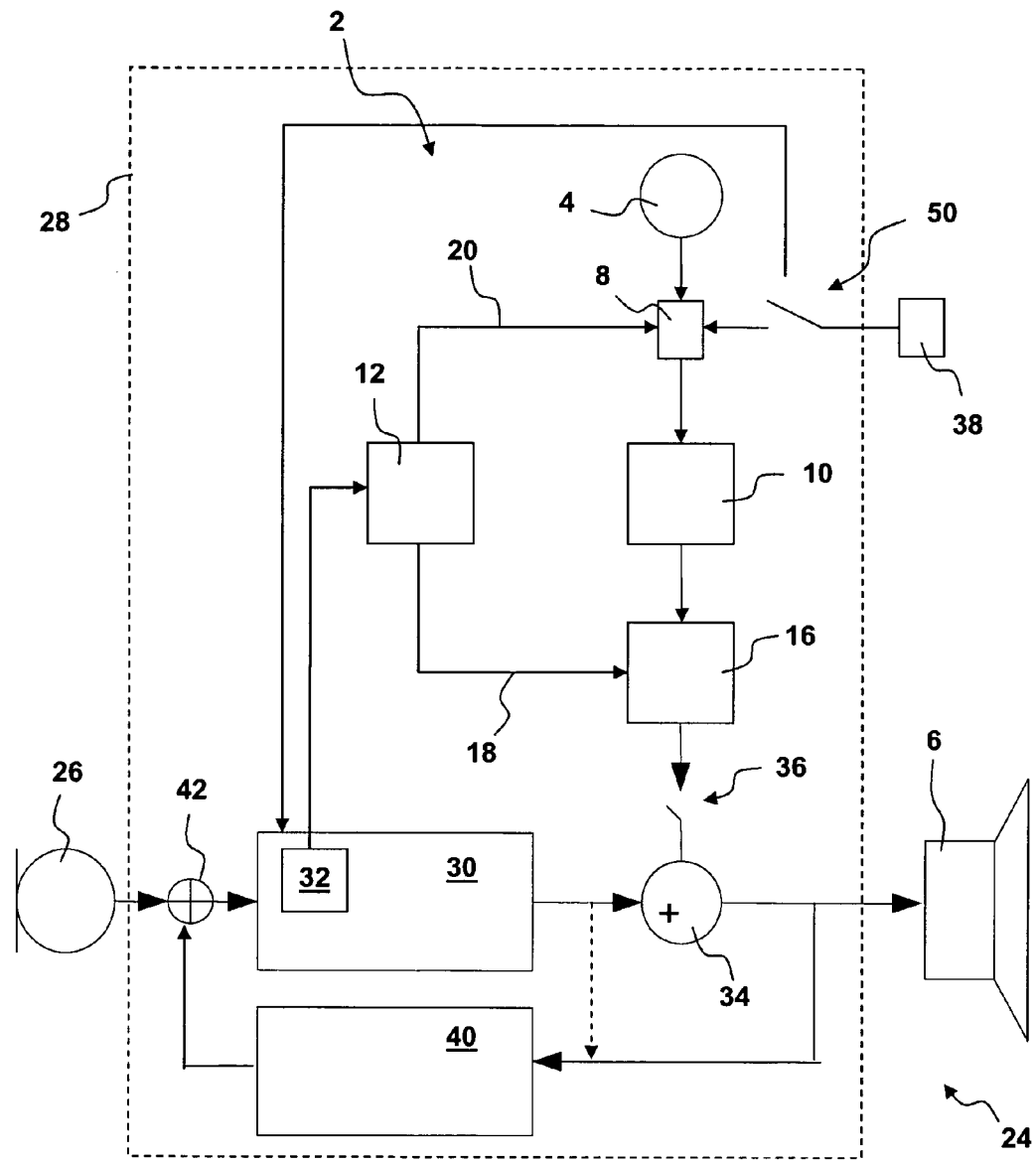
Figure 10:
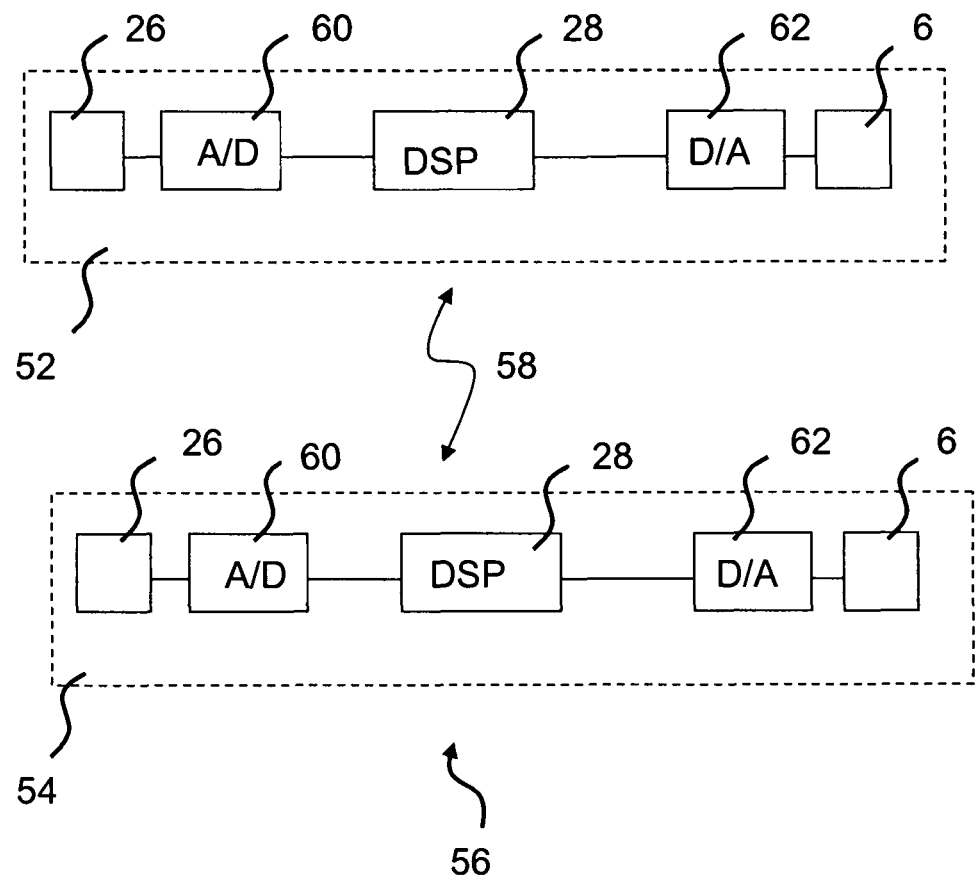
Figure 11:
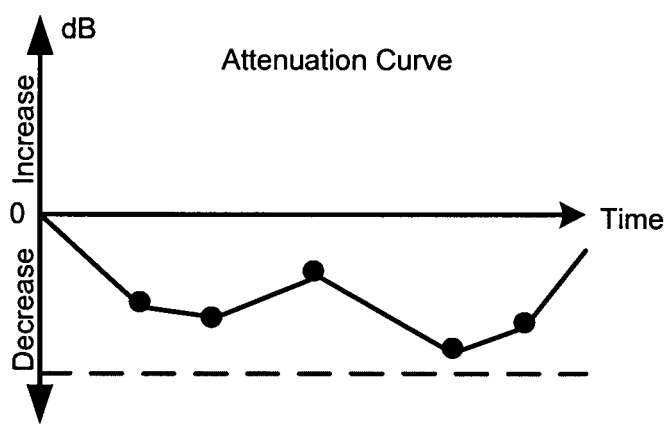

In the following, the embodiments are explained in more detail with reference to the drawings, wherein FIG. 1 shows a simplified block diagram of a sound enrichment system according to some embodiments, FIG. 2 is a block diagram illustrating an embodiment of a sound enrichment system with a separate signal modulator, FIG. 3 is a block diagram illustrating an alternative embodiment of a sound enrichment system, FIG. 4 is a block diagram illustrating yet another embodiment of a sound enrichment system, FIG. 5 is a block diagram illustrating yet another alternative embodiment of a sound enrichment system, FIG. 6 shows one embodiment of a sound enrichment system forming part of a hearing aid, FIG. 7 shows an alternative embodiment of a sound enrichment system forming part of a hearing aid, FIG. 8 shows a simplified flow diagram of a method of providing a noise enriched sound signal for the provision of relief of tinnitus, FIG. 9 shows an alternative embodiment of a sound enrichment system forming part of a hearing aid, FIG. 10 schematically illustrates a binaural hearing aid system according to some embodiments, and FIG. 11 shows an example of an attenuation curve for amplitude modulations of a noise signal as function of time.

DETAIL DESCRIPTION

The embodiments will now be described more fully hereinafter with reference to the accompanying drawings. The claimed invention may, however, be embodied in different forms and should not be construed as limited to the embodiments set forth herein. Thus, the illustrated embodiments are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated. Like reference numerals refer to like elements throughout.

FIG. 1 shows a simplified block diagram of a sound enrichment system 2 according to some embodiments. The sound enrichment system 2 comprises a noise generator 4 for the provision of a noise signal having a certain average signal level. Also shown is an output transducer 6 that is configured to convert the noise signal to an acoustic signal that during use of the sound enrichment system 2 is presented to a user. As used in this specification, the term "noise signal" is not limited to the signal that is generated by the noise generator 4, and may refer to a modified signal that is derived from the signal generated by the noise generator 4. For example, the noise signal may be obtained by processing (e.g., delaying, factoring, filtering, modifying, etc.) the signal from the noise generator 4. The sound enrichment system 2 further comprises at least one signal modulator (not shown) that forms an integrated part of the noise generator 4. The signal modulator (not shown) is configured to randomly or pseudo-randomly modulate the noise signal to obtain a modulated noise signal. As used in this specification, the term "modulated noise signal" is not limited to the output signal from the signal modulator, and may refer to a modified signal that is derived from the signal output of the signal modulator. For example, the modulated noise signal may be obtained by processing (e.g., delaying, factoring, filtering, modifying, etc.) the signal output from the signal modulator. The integrated noise generator 4 and signal modulator (not shown) are thus configured to generate a random or pseudo-random modulated noise signal. The sound enrichment system 2 comprises furthermore an (optional) signal level adjuster 8, whereby the level of the noise signal may be adjusted. The signal level of the noise signal may for example be adjusted by the signal level adjuster 8 in dependence of a specific hearing loss of a user of the sound enrichment system 2, and/or the signal level of the noise signal may for example be adjusted in dependence of the type of the perceived tinnitus of a user of the sound enrichment system 2.

In order to account for nonlinearities in the output transducer 6, the sound enrichment system 2 may (optionally) comprise a receiver response equalization filter 10. Scientific investigations have, however, shown that in some practical implementations a receiver response equalization filter 10 may not be needed.

FIG. 2 is a block diagram illustrating an embodiment of the sound enrichment system 2 that comprises a separate signal modulator 12. The signal modulator 12 is configured to randomly or pseudo-randomly modulate the noise signal that is generated by the noise generator 4. In one embodiment of the sound enrichment system 2, the signal modulator 12 is configured to modulate the amplitude of the noise signal. In an alternative embodiment of the sound enrichment system 2, the signal modulator 12 is configured to modulate selected spectral characteristics of the noise signal. In yet an alternative embodiment of the sound enrichment system 2, the signal modulator 12 is configured to modulate both the amplitude and selected spectral characteristics of the noise signal.

FIG. 3 is a block diagram illustrating an alternative embodiment of the sound enrichment system shown in FIG. 2, wherein the signal modulator 12 modulates the noise signal, generated by the noise generator 4, by generating a randomly or pseudo-randomly varying modulation signal 14 for multiplication with the noise signal in the multiplier 22.

FIG. 4 is a block diagram illustrating yet another embodiment of the sound enrichment system 2 that comprises a spectral shaping filter 16 for (at least in part) filtering the noise signal, and wherein the at least one modulator 12 modulates selected spectral characteristics of the noise signal by a variation of the frequency response of the spectral shaping filter 16. Preferably, the signal modulator 12 generates a randomly or pseudo-randomly varying modulation signal 18 that is used to modulate the frequency response of the spectral shaping filter 16.

FIG. 5 is a block diagram illustrating yet another alternative embodiment of a sound enrichment system 2, wherein the modulator 12 generates two modulation signals, 18 and 20. The modulation signals 18 and 20 are preferably random or pseudo-random signals. In a preferred embodiment, the modulation signals 18 and 20 are generated independently of each other by the modulator 12. The signal 20 is used to modulate the amplitude of the noise signal, and the modulation signal 18 is used to modulate selected spectral characteristics of the noise signal by varying the frequency response of the spectral shaping filter 16. The modulation signals 18 and 20 are preferably different from each other and operate at different rates.

Note that any of the blocks illustrated in FIGS. 1-5 situated between the noise generator 4 and the output transducer 6 may be placed in any order.

The sound enrichment system 2 illustrated in any of the FIGS. 1-5 (preferably excluding the output transducer 6) may be provided as a personal portable device that is configured for being linked with at least one hearing aid, such as a single hearing aid or a binaural hearing aid system. Preferably, such a link is wireless, but the link may in an embodiment be wired.

FIG. 6 shows one embodiment of a sound enrichment system 2 forming part of a hearing aid 24. The hearing aid 24 comprises a microphone 26 for the provision of an input signal, a signal processor 28 that is configured to process the input signal according to a hearing impairment compensation algorithm in a hearing impairment compensation block 30, in order to provide a hearing impairment corrected output signal. The hearing aid further comprises an output transducer 6 (sometimes referred to as a receiver) that is configured to convert the hearing impairment corrected output signal into an acoustical signal that during use of the hearing aid is presented to a user. Here, the output transducer 6 of the sound enrichment system 2 is the output transducer of the hearing aid 24. The components of the sound enrichment system 2, thus forms an integral part of the hearing aid 24. The other components of the sound enrichment system 2 such as, the noise generator 4, the (optional) level adjuster 8, the (optional) receiver response equalization filter 10, the spectral shaping filter 16, and the signal modulator 12 (which signal modulator 12 in an alternative embodiment may form a part of the noise generator) may all be implemented in a software program stored on a machine readable data storage device which is executable on a processing device, such as for example the signal processor 28. Hereby is achieved that the main parts of the sound enrichment system 2 may be provided as an add-on software program to the general hearing aid software package (software implementations of hearing aid algorithms). Alternatively, only some of the components mentioned above may be implemented in a software program. For example the noise generator 4 and/or the signal modulator 12 may be implemented in a software program stored on a machine readable data storage device which when executed on a processing device, such as the signal processor 28, is configured to generate the modulated noise signal, and wherein the other components, such as the (optional) level adjuster 8, the (optional) receiver response equalization filter 10, and the spectral shaping filter 16 may be implemented in hardware. However, in a preferred embodiment, the spectral shaping filter 16 is implemented in a software program. In an embodiment, a software program stored on a machine readable data storage device comprises an implementation of the noise generator 4 and the signal modulator 12.

The modulated noise signal may be connected to adder 34 by the switch 36. The switch 36 may be implemented in software. Thus, when, during use, the switch 36 is enabled, the modulated noise signal will be added to the hearing impairment corrected output signal, and then subsequently converted to an acoustical noise signal in the transducer 6. The switch 36 may in one embodiment be controllable by a physical switch, like for example a toggle wheel or another form of mechanical or electrical (or optionally magnetic, magneto-resistive or giant magneto-resistive) contact in or on the hearing aid 24. Alternatively, the switch 36 may be software controlled. Such a software controlled switch 36 may for example be enabled or disabled by a user of the hearing aid 24, by a suitable choice of program(s) (usually a hearing aid user has the possibilities of choosing between a number of different programs, typically around 2-6 different programs).

For many tinnitus sufferers, the perceived tinnitus may be a highly time varying phenomenon. Some investigations show that this time variations may be stress related. Thus, in one embodiment, the (optional) signal level adjuster 8 may, during use, be controlled by the volume control 38 of the hearing aid 24, the volume control 38 being adjustable by a user. This enables the user to adjust the level of the generated noise signal in dependence of the possibly time varying perceived tinnitus. Alternatively, the level adjuster may not be user controlled, but instead be adjusted to a default level (which would be adequate for some users), or individually adjusted by a professional in order to, during use, optimally provide the signal level needed for the noise signal in order to provide optimal relief of the perceived tinnitus of a user of the hearing aid 24.

Each (or any) of the embodiments of a sound enrichment system 2 shown in FIGS. 1-5 may form part of a hearing aid. Any of the blocks shown in FIGS. 1-5, preferably except the output transducer 6, may either individually or in any combination be implemented in a software product.

The at least one modulator 12 is configured to modulate the amplitude and/or the spectral characteristics of the noise signal. The modulator 12 is operatively connected to the signal path of the noise signal. Preferably the modulator 12 is operatively connected to the signal level adjuster 8. The modulator 12 may be configured to generate a randomly or pseudo-randomly varying amplitude modulation signal 20 that is multiplied to the noise signal, whereby amplitude modulation of the noise signal is achieved. Preferably, the modulator 12 is operatively connected to the signal level adjuster 8, whereby it is achieved that both an overall level adjustment of the noise signal and an amplitude modulation of the noise signal is achieved. The modulator 12 is furthermore operatively connected to the spectral shaping filter 16, the modulator 12 being configured to generate a randomly or pseudo-randomly varying spectral modulation signal 18 that is used as a control signal to randomly or pseudo-randomly vary selected spectral characteristics of the noise signal by a variation of the frequency response of the spectral shaping filter 16. In an alternative embodiment, the modulator 12 may be configured to only modulate either the amplitude or the spectral characteristics of the noise signal. In yet an alternative embodiment the modulator 12 may be configured to modulate the amplitude and spectral characteristics of the noise signal in steps subsequently after each other. The modulator 12 may in an alternative embodiment comprise two separate autonomous units.

The spectral shaping filter shown in FIG. 4 or FIG. 5 or FIG. 6 (or FIG. 7 described below or FIG. 9 described below) may comprise a band-pass filter, preferably a low-pass filter and a high-pass filter, for example such as IIR Butterworth filter(s) of second or third order or Chebychev filter(s).

The sound enrichment system 2 forming part of the hearing aid 24 may comprise a classifier 32. The classifier may form a part of the hearing impairment compensation block 30, which further may comprise a compressor (not shown). The hearing impairment compensation block 30 may partly be implemented in hardware and partly implemented in software. The classifier 32 may be operatively connected to the modulator 12, whereby is achieved that the modulation of the amplitude and/or spectral characteristics of the noise signal may be performed in dependence of a classification of the ambient sound environment. For example if there is noise present in the ambient sound environment then the modulation of the amplitude and/or spectral characteristics of the noise signal may be performed in such a way that the ambient noise level may in part be used in the sound enrichment. Alternatively, the classifier 32 may be directly operatively connected to the noise level adjuster 8 (direct connection not shown). Hereby is achieved that the level of the noise signal may be directly adjusted in dependence of a classification of the ambient sound environment. Since speech usually is a sound that is desirable for a user of the hearing aid 24 to hear, the generation of the noise signal may for example be turned off if speech is present in the ambient sound environment. In yet an alternative embodiment, the classifier 32 may be directly operatively connected to the spectral shaping filter 16 (direct connection not shown).

As mentioned before, scientific investigations show that, sound enrichment in openly fitted hearing aids is especially advantageous in order to achieve optimal habituation of a user's perceived tinnitus in a short period of time (typically a period of time below 8 months to 1 year). Some of the sound that is emitted by the output transducer 6 may leak back to the microphone 26 and then be amplified again in the hearing impairment compensation block 30. This problem is commonly referred to as feedback. This feedback problem is bigger in openly fitted hearing aids than more traditional hearing aids. Thus, in a preferred embodiment, the hearing aid 24 is configured to be openly fitted to a user, and furthermore comprise a feedback cancellation filter 40 that filters the output signal of the hearing impairment compensation block 30 and subtracts it from the input signal from the microphone 26 in the adder 42. The input to the feedback cancellation filter 40 may in one embodiment of the hearing aid 24 be tapped after the adder 34, and in an alternative embodiment tapped before the adder 34 as indicated by the dotted arrow 43.

FIG. 7 shows an alternative embodiment of a sound enrichment system 2 forming part of a hearing aid 24. The embodiment shown in FIG. 7 is essentially similar to the embodiment shown in FIG. 6, thus only the difference between them will be described. The difference between the embodiment shown in FIG. 7 as compared to the embodiment shown in FIG. 6, is that in FIG. 7 the classifier 32 does not form a part of the hearing impairment compensation block 30, but is implemented as an integral part of the sound enrichment system 2. The classifier 32 may in an alternative embodiment furthermore be operatively connected (not shown) to the hearing impairment compensation block 30. The classifier may be a neural network based classifier, a hidden Markov model classifier, or any other kind of classifier known in the art. The classifier 32 shown in FIG. 6 or FIG. 7 may be implemented in a software program.

FIG. 8 shows a simplified flow diagram of a method of providing a noise enriched sound signal for the provision of relief of tinnitus, the method comprising a step 44 of generating a noise signal, a step 46 of randomly or pseudo-randomly modulating (or adjusting) the noise signal, and a step 48 of generating an acoustic noise signal from the modulated noise signal, wherein the acoustic noise signal during use of the method is presented to a tinnitus suffering person. The step 46 of modulating the noise signal may comprise the sub steps of modulating the amplitude and/or selected spectral characteristics of the noise signal.

FIG. 9 shows an embodiment of a sound enrichment system 2 forming part of a hearing aid 24. The embodiment shown in FIG. 9 is essentially similar to the embodiment shown in FIG. 6, thus only the difference between them will be described. A difference between the embodiment shown in FIG. 9 and the embodiment shown in FIG. 6 is that the embodiment illustrated in FIG. 9 comprises a switch 50. The switch 50 may be implemented in software. In the embodiment illustrated in FIG. 9, the switch 50 has two positions, one wherein the volume control 38 is connected to the hearing impairment processing block 30, and another wherein the volume control 38 is connected to the signal level adjuster 8. Hereby, the volume control 38 can be switched between a position wherein the volume control 38 can be used to control the level of the noise signal generated by the noise generator 4, and a position wherein the volume control 38 can be used to control the level of the hearing aid gain that is applied in the hearing impairment compensation block 30. The switch 50 may in one embodiment be controllable by a physical switch, like for example a toggle wheel or another form of mechanical or electrical (or optionally magnetic, magneto-resistive or giant magneto-resistive) contact in or on the hearing aid 24. Alternatively, the switch 50 may be software controlled. Such a software controlled switch 50 may for example be enabled or disabled by a user of the hearing aid 24, by a suitable choice of program(s). Instead of two distinct positions for the switch 50, it may also be implemented as a "soft switch" that works in such a way that the volume control may be partly connected to the hearing impairment compensation block 30, and partly connected to the signal level adjuster 8. In an embodiment, the switch 50 may be operatively connected to the classifier 32, such that the adjustment of the switch 50 is performed in dependence of a classification of the ambient sound environment. For example if it is determined in the classifier 32 that the ambient sound environment is substantially quiet, then the switch 50 may be automatically switched to a position, wherein the volume control 38 will be connected to the level adjuster 8. This is due to the fact that a user may have greater benefit from using the volume control to adjust the signal level of the noise signal when the ambient environment is substantially quiet. Analogous, if it is determined in the classifier 32 that the ambient sound environment comprises speech then the switch 50 may be automatically switched to a position, wherein the volume control 38 will be connected to the hearing impairment compensation block 30. This is due to the fact that a user may have greater benefit from using the volume control to adjust the gain of the hearing aid 24 when the ambient environment comprises speech.

The switch 50 may be operatively connected to the switch 36, or to the noise generator 4, or to the modulator 12, such that the volume control may be used to control the sound enrichment system, i.e. to control whether the noise generator 4 is active or not, or whether the switch 36 is enabled or not, i.e. whether the noise signal generated by the sound enrichment system is added to the output signal from the hearing impairment compensation block 30 in the adder 34.

In an embodiment, the switch 50 as described with reference to FIG. 9 above may be implemented in a hearing aid as shown in FIG. 7.

In an embodiment of a sound enrichment system 2 forming part of a hearing aid 24 (illustrated in FIG. 6, FIG. 7, and FIG. 9) as well as an embodiment of a hearing aid 24 comprising a sound enrichment system 2, the modulated noise signal generated by the sound enrichment system 2 may be connected to an input of the hearing impairment correction block 30, e.g. by adding the modulated noise signal to the signal from the microphone 26 just before entering into the hearing impairment correction block. Such an implementation may replace the implementation illustrated in FIG. 6, FIG. 7, and FIG. 9, respectively, by the adder 34.

FIG. 10 schematically illustrates a binaural hearing aid system 56 according to some embodiments. The binaural hearing aid system 56 comprises a first hearing aid 52 and a second hearing aid 54.

The first hearing aid 52 comprises microphone 26 for the provision of a first input signal, an A/D converter 60 for converting the first input signal into a first digital input signal, a digital signal processor (DSP) 28 that is configured to process the digitalized first input signal, a D/A converter 62 for converting the processed first digital input signal into a first analogue output signal. The first analogue output signal is then transformed into a first acoustical output signal (to be presented to a first ear of a user) in a receiver 6.

Similarly the second hearing aid 54 comprises a microphone 26 for the provision of a second input signal, an A/D converter 60 for converting the second input signal into a second digital input signal, a digital signal processor (DSP) 28 that is configured to process the digitalized second input signal, a D/A converter 62 for converting the processed second digital input signal into a second analogue output signal. The second analogue output signal is then transformed into a second acoustical output signal (to be presented to a second ear of a user) in a receiver 6.

The binaural hearing aid system 56 furthermore comprises an (optional) link 58, between the two individual hearing aids 52 and 54. The link 58 is preferably wireless, but may in another embodiment be wired. The link 58 enables at least one of the two hearing aids 52 and 54 to communicate with the other, i.e. it may be possible to send information from at least one of the two hearing aids 52 and 54 via the link 58 to the other of the two hearing aids 52 or 54. In a preferred embodiment, the link 58 enables the two hearing aids 52 and 54 to communicate with each other. The link 58, thus, enables the two digital signal processors (both denoted 28 in FIG. 10), to perform binaural signal processing. Moreover, the link 58 enables the two hearing aids 52 and 54 to perform the modulations of the noise signals generated in the two hearing aids 52 and 54 in a coordinated manner. At least one of the hearing aids 52 or 54 comprises a sound enrichment system 2. Preferably, both of the hearing aids 52 and 54 comprise a sound enrichment system 2.

In a preferred embodiment, the first and second hearing aids 52, 54 are the hearing aid 24 shown in FIG. 6, 7, or 9. Hereby, it is achieved that the modulations of the amplitude and/or selected spectral characteristics of the noise signal may furthermore be performed in a coordinated, possibly asynchronous, manner between the two hearing aids 52 and 54. The modulations could for example comprise amplitude modulations and modulations of band pass filtering in the two hearing aids 52 and 54. Slightly asynchronous relations between the amplitude envelope and frequency band pass filtering between the two hearing aids 52 and 54 could make the modulated noise signal sound much like listening to breaking waves, as if the user of the binaural hearing aid system 56 was standing on a beach and listening to the waves. This way an even more comfortable noise signal for tinnitus relief is provided for. Alternatively or additionally, the modulations in the first hearing aid 52, could comprise amplitude modulations of the generated noise signal, and the modulations of the noise signal in the second hearing aid 54 could comprise modulations of selected spectral characteristics of the generated noise signal. The modulations of the amplitude and selected spectral characteristics of the noise signal may even be shifted between the two hearing aids 52 and 54, so that for example the first hearing aid 52 starts in a mode wherein it generates an amplitude modulated noise signal while the second hearing aid 54 generates a noise signal, wherein selected spectral characteristics of a noise signal is modulated. After a certain time span the roles of the two hearing aids 52 and 54 are reversed. This shifting between the modes of the two hearing aids 52 and 54 may continue as long as they are turned on, and the time span between the shifting may also be a randomly determined time span, or even be a time span that is modulated by another signal.

The hearing aids 52 and 54 forming part of the binaural hearing aid system 56 may in one embodiment be configured to operate in a master-slave configuration. In an embodiment of the binaural hearing aid system 56, the two hearing aids 52 and 54 are configured to operate in a master-slave configuration, and wherein only one of the two hearing aids 52 and 54 comprises a sound enrichment system 2. Hereby is achieved an embodiment wherein all the signal processing associated with the generation and modulation of the noise signal and the classification of the sound environment may be done in only one of the two hearing aids 52 or 54, and the wherein the thus modulated noise signal may simply be transferred to the other via the link 58. However, in a preferred embodiment, both hearing aids 52 and 54 comprise a sound enrichment system 2. Hereby is achieved that only signals used to control the sound enrichment system may need to be transferred from the master to the slave. This will lead to a considerable saving of the energy usage, because it may require at least five times as much battery power to transfer the noise signals itself from the master to the slave. It is furthermore, understood that in one embodiment of the binaural hearing aid system 56 only one of the two hearing aids 52 or 54, preferably the one of the hearing aids 52 or 54 that is configured as the master hearing aid, is equipped with a volume control 38 and possibly also a switch 50 as described above with reference to the embodiments shown in FIGS. 6, 7 and 9, and wherein the chosen (automatically or manually chosen) volume settings is automatically applied to the other hearing aid as well, via the link 58.

In yet another preferred embodiment of the binaural hearing aid system 56 according, each of the two individual hearing aids 52 and 54 forming part of the binaural hearing aid system 56 comprises a sound enrichment system 2, and each of them comprises a volume control, wherein the volume control of one of the hearing aids 52 or 54 is used to control the hearing aid gain in both hearing aids 52 and 54, and the volume control of the other hearing aid 52 or 54 is used to control the signal level of the noise signal generated by the sound enrichment system 2, in both hearing aids 52 and 54. Hereby is achieved a binaural hearing aid configuration, wherein the volume control on for example the left hearing aid may be used to control the hearing aid gain of both the left and the right hearing aid (via the link 58), and wherein the volume control on for example the right hearing aid may be used to control the hearing aid gain of both the right and the left hearing aid (via the link 58). Thus, only one volume control on each hearing aid is necessary in order to control the two features (hearing aid gain and level of the noise signal generated for the relief of tinnitus) of the binaural hearing aid system. Besides, it may not be needed that the volume control is configured to be switched between controlling the two features mentioned above.

FIG. 11 shows an example of an attenuation curve provided by the signal modulator 12 for amplitude modulations of noise signal as function of time. According to the illustrated example the signal modulator 12 calculates an attenuation curve that can be applied to the noise signal that is generated by the noise generator 4 in order to obtain a less monotonic noise signal. The signal modulator 12 may be configured in a number of ways to provide an attenuation curve which fits the user's requirements. For example the signal modulator 12 can be configured with the following properties: A curve attenuation level (chosen from en event space of modulation values) and a curve time period, also generally referred to as a modulation period (chosen from an event space of modulation periods).

The solid circles in FIG. 11 indicate a transition node. Each transition node is defined by the following properties: An attenuation level and a time span to the previous node in time. The time span from one node to the previous node in time is in an embodiment the modulation period. The attenuation level (also referred to as the modulation value) may be chosen by: Either setting the level of attenuation randomly or pseudo-randomly or by setting it to a fixed attenuation value, and similarly the time span to the previous node may be chosen by: Setting the time span to a random or pseudo-random value or by setting it to a fixed time span. The range of possible attenuation levels may be chosen from an event space of modulation values, and similarly the range of possible time spans between two successive nodes may be chosen from an event space of modulation periods.

In a preferred embodiment, the range of possible attenuation levels is limited, i.e., the event space of modulation values is preferably limited. For example it may be limited to attenuation levels in the range of 0 dB-20 dB, or 0 dB-15 dB, or 0 dB-12 dB, or alternatively to 0 dB-10 dB. In these mentioned examples the maximum level the attenuation may take is 20 dB, 15 dB, 12 dB or 10 dB, respectively. In FIG. 11 the dashed line illustrates an example of a maximum level of attenuation that can be applied by a modulator 12. Similarly, the time span between two successive nodes may be limited, i.e. the event space of modulation periods may be limited. For example it may be limited to time spans of 0-20 seconds, 1-15 seconds, 2-10 seconds or 2-8 seconds. Hereby is achieved an embodiment, wherein the modulator 12 may be configured to modulate the noise signal according to a method comprising the steps of: Randomly or pseudo-randomly choosing a modulation value from an event space of modulation values, and randomly or pseudo-randomly choosing a modulation period from an event space of modulation periods, i.e. a dual randomization may be achieved, because both the attenuation level, i.e. modulation value and the time span between two successive nodes, i.e. the modulation period, is randomly or pseudo-randomly chosen from the respective event spaces of modulation values and modulation periods, respectively.

Preferably, the hearing aid 24, 52, 54 processes sound signals in blocks of a certain number of samples, wherein the time distance between the samples is 1 divided by the sample frequency. As mentioned before the solid circles in FIG. 11 indicates a transition node. At these points in time a new set of parameters for the modulator 12 is found, i.e. a new time span and a new attenuation level. The time span between two transition nodes may correspond to several blocks being processed in the hearing aid 24, 52, 54. Thus a block counter variable may be used to keep track on when a time span has elapsed, thereby requiring a new set of parameters for the modulator 12 to be found.

The description of the amplitude modulations with reference to FIG. 11 may analogously be applied to the modulations of selected spectral characteristics of the noise signal. It is furthermore understood that the modulations as described with reference to FIG. 11 may be utilized in any other embodiments described in the present patent application, for example with reference to any of the embodiments shown in any of the other figures.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The claimed inventions are intended to cover alternatives, modifications, and equivalents.

LIST OF REFERENCES

In the following is given a list of reference numbers that are used in the detailed description.

2 sound enrichment system,
4 noise generator,
6 output transducer,
8 signal level adjuster,
10 receiver response equalization filter,
12 modulator,
14, 18, 20 randomly or pseudo-randomly varying modulation signal,
16 spectral shaping filter,
22 multiplier,
24, 52, 54 hearing aid,
26 microphone,
28 signal processor, 30 hearing impairment compensation block,
32 environment classifier,
34 adder,
36 switch,
38 volume control,
40 feedback cancellation filter,
42 adder,
43 alternative input signal to the feedback cancellation filter,
44 method step of generating a noise signal,
46 method step of modulating a noise signal,
48 method step of generating an acoustic noise signal,
50 switch for volume control,
56 a binaural hearing aid system,
58 wireless link,
60 A/D converter, and
62 D/A converter.

The invention claimed is:

1. A sound enrichment system for provision of tinnitus relief, the sound enrichment system comprising:
a noise generator;
at least one signal modulator configured to perform an adjustment of a noise signal to obtain an adjusted noise signal, wherein the at least one signal modulator is configured to perform the adjustment of the noise signal at a rate that is slower than a rate of amplitude variation in the noise signal by a factor of at least ten, the noise signal obtained using the noise generator;
an output transducer for conversion of the adjusted noise signal to an acoustic signal for presentation to a user; and
a microphone;
wherein the output transducer and the microphone are parts of a hearing aid.

2. The sound enrichment system according to claim 1, wherein the at least one signal modulator is configured to randomly or pseudo-randomly choose a modulation value from an event space of modulation values.

3. The sound enrichment system according to claim 1, wherein the at least one signal modulator is configured to randomly or pseudo-randomly choose a modulation period from an event space of modulation periods.

4. The sound enrichment system according to claim 1, wherein the at least one signal modulator is configured to modulate an amplitude of the noise signal.

5. The sound enrichment system according to claim 1, wherein the at least one signal modulator is configured to modulate spectral characteristics of the noise signal.

6. The sound enrichment system according to claim 5, wherein the at least one signal modulator is configured to modulate the spectral characteristics of the noise signal at a rate that is slower than a rate of a variation of the spectral characteristics in the noise signal.

7. The sound enrichment system according to claim 5, further comprising a spectral shaping filter for at least in part filtering the noise signal, wherein the at least one signal modulator is configured to modulate the spectral characteristics of the noise signal by modulating a frequency response of the spectral shaping filter.

8. The sound enrichment system according to claim 7, wherein the modulation of the frequency response of the spectral shaping filter comprises a modulation of at least one parameter selected from the group consisting of a Stop-band frequency, a slope, a number of poles and zeroes, and a location of poles and zeroes.

9. The sound enrichment system according to claim 1, further comprising an environment classifier for determining a classification of an ambient sound environment of the sound enrichment system, wherein the at least one signal modulator is configured to adjust the noise signal based at least in part on the classification of the ambient sound environment of the sound enrichment system.

10. The sound enrichment system according to claim 9, wherein the at least one signal modulator is configured to adjust the noise signal based at least in part on whether or not speech is present in the ambient sound environment.

11. The sound enrichment system according to claim 9, wherein the environment classifier comprises a speech detector.

12. The sound enrichment system according to claim 1, wherein the noise generator is a part of the hearing aid.

13. The sound enrichment system according to claim 12, wherein the hearing aid is configured for use by an ear of the user.

14. The sound enrichment system according to claim 12, wherein the hearing aid comprises a volume control that has a first mode of operation in which the volume control is operable to control a noise signal level, and a second mode of operation in which the volume control is operable to control a hearing aid gain.

15. The sound enrichment system according to claim 14, further comprising a switch for allowing the user to switch between the first and second modes of operation.

16. The sound enrichment system according to claim 14, wherein the volume control is capable of being switched between the first and second modes of operation based at least in part on a classification of an ambient sound environment of the hearing aid.

17. The sound enrichment system according to claim 14, wherein the volume control is capable of being switched automatically between the first and second modes of operation.

18. The sound enrichment system of claim 1, wherein the hearing aid comprises a first hearing aid, wherein the at least one signal modulator comprises a first signal modulator, wherein the noise generator, the output transducer, and the first signal modulator are parts of the first hearing aid, and wherein the sound enrichment system further includes a second hearing aid having an additional noise generator, an additional output transducer, and a second signal modulator.

19. The sound enrichment system of claim 18, wherein the first and second hearing aid are operatively connected to each other, and wherein the first signal modulator in the first hearing aid and the second signal modulator in the second hearing aid are configured to operate with each other in a coordinated manner.

20. The sound enrichment system of claim 1, wherein at least a part of the noise generator and at least a part of the at least one signal modulator are implemented using a software program.

21. The sound enrichment system of claim 1, wherein the at least one signal modulator is a part of the noise generator.

22. The sound enrichment system of claim 1, further comprising a multiplier coupled to the at least one signal modulator.

23. The sound enrichment system of claim 1, further comprising a spectral shaping filter coupled to the at least one signal modulator.

24. The sound enrichment system of claim 23, further comprising a multiplier, wherein the at least one signal modulator is coupled to both the multiplier and the spectral shaping filter.

25. The sound enrichment system of claim 1, wherein the noise signal comprises a signal generated by the noise generator.

26. The sound enrichment system of claim 1, wherein the noise signal is derived from a signal generated by the noise generator.

27. The sound enrichment system according to claim 1, wherein the acoustic signal has a characteristic suitable for relieving tinnitus.

28. The sound enrichment system of claim 1, wherein the at least one signal modulator is configured to adjust the noise signal randomly at the rate that is slower than the rate of the amplitude variation in the noise signal.

29. A method of providing a noise enriched sound signal for provision of relief of tinnitus, the method comprising:
  generating a noise signal;
  modulating the generated noise signal to obtain a modulated noise signal, wherein a rate at which the noise signal is modulated is slower than a rate of amplitude variation in the noise signal by a factor of at least ten; and
  generating an acoustic signal using the modulated noise signal for presentation to a user;
  wherein the act of generating the acoustic signal is performed using a transducer that is a part of a hearing aid having a microphone.

30. The method of claim 29, wherein the modulated noise signal comprises a randomly or pseudo randomly modulated noise signal.

31. The method of claim 29, wherein the act of modulating the generated noise signal is performed randomly or pseudo randomly after the noise signal is generated.

32. The method of claim 29, wherein the acoustic signal has a characteristic suitable for relieving tinnitus.

33. The method of claim 29, wherein the noise signal is modulated randomly at the rate that is slower than the rate of the amplitude variation in the noise signal.

34. A sound enrichment system for provision of tinnitus relief, the sound enrichment system comprising:
  a noise generator;
  at least one signal modulator configured to perform an adjustment of a noise signal to obtain an adjusted noise signal, the noise signal obtained using the noise generator, the noise signal comprising a white or color noise, wherein the at least one signal modulator is configured to perform the adjustment of the noise signal randomly, and wherein the at least one signal modulator is configured to perform the adjustment of the noise signal at a rate that is slower than a rate of an amplitude variation in the noise signal; and
  an output transducer for conversion of the adjusted noise signal to obtain an acoustic signal for presentation to a user.

35. The sound enrichment system according to claim 34, wherein the at least one signal modulator is configured to adjust the noise signal by performing a random or a pseudo-random modulation on the noise signal.

36. The sound enrichment system according to claim 34, wherein the at least one signal modulator is configured to adjust the noise signal by performing a modulation of spectral characteristics of the noise signal.

37. The sound enrichment system according to claim 36, wherein the at least one signal modulator is configured to perform the modulation at a rate that is slower than a rate of a variation of the spectral characteristics in the noise signal.

38. The sound enrichment system according to claim 36, further comprising a spectral shaping filter for at least in part filtering the noise signal, wherein the modulation of the spectral characteristics of the noise signal comprises a modulation of a frequency response of the spectral shaping filter.

39. The sound enrichment system according to claim 7, wherein the modulation of the frequency response of the spectral shaping filter comprises a modulation of at least one parameter selected from the group consisting of a Stop-band frequency, a slope, a number of poles and zeroes, and a location of poles and zeroes.

40. The sound enrichment system according to claim 34, wherein the output transducer is a part of a hearing aid.

41. The sound enrichment system according to claim 40, wherein the hearing aid comprises a control that has a first mode of operation in which the control is operable to control a noise signal level, and a second mode of operation in which the control is operable to control a hearing aid gain.

42. The sound enrichment system according to claim 41, further comprising a switch for allowing the user to switch between the first and second modes of operations.

43. The sound enrichment system according to claim 41, wherein the control is capable of being switched between the first and second modes of operation based at least in part on the output from a microphone.

44. The sound enrichment system according to claim 34, wherein the at least one signal modulator is configured to adjust the noise signal and to obtain the adjusted noise signal based at least in part on an analysis of an output from a microphone.

45. The sound enrichment system according to claim 44, wherein the at least one signal modulator is a part of a processing system that is configured to perform the analysis of the output from the microphone.

46. The sound enrichment system according to claim 34, wherein the at least one signal modulator is a part of a processing system.

47. The sound enrichment system according to claim 46, wherein the processing system comprises a multiplier.

48. The sound enrichment system according to claim 46, wherein the processing system comprises a spectral shaping filter.

49. The sound enrichment system according to claim 48, further comprising a multiplier, wherein the at least one signal modulator is coupled to both the multiplier and the spectral shaping filter.

50. The sound enrichment system according to claim 46, wherein the processing system comprises a signal level adjustor.

51. The sound enrichment system according to claim 46, wherein the processing system comprises a receiver response equalization filter.

52. The sound enrichment system according to claim 34, wherein the at least one signal modulator comprises a first signal modulator, wherein the noise generator, the first signal modulator, and the output transducer are parts of a first hearing aid, and wherein the sound enrichment system further includes a second hearing aid having an additional noise generator, a second signal modulator, and an additional output transducer.

53. The sound enrichment system according to claim 52, wherein the first and second hearing aid are operatively connected to each other, and wherein the first signal modulator in the first hearing aid and the second signal modulator in the second hearing aid are configured to operate with each other in a coordinated manner.

54. The sound enrichment system according to claim 34, wherein at least a part of the noise generator is implemented using a software program.

55. The sound enrichment system according to claim 34, further comprising a detector configured to detect a characteristic of an environment and generate an output;
wherein the at least one signal modulator is configured to obtain the adjusted noise signal based at least in part on the output from the detector.

56. The sound enrichment system according to claim 55, wherein the detector is configured to generate the output based on the detected characteristic of the environment.

57. The sound enrichment system according to claim 55, wherein the detector is configured to generate the output having a first value when the environment has a first characteristic, and to generate the output having a second value when the environment has a second characteristic.

58. The sound enrichment system according to claim 55, wherein the detector comprises a microphone, and the characteristic of the environment comprises sound from the environment.

59. The sound enrichment system according to claim 34, wherein the at least one signal modulator is configured for adjusting the noise signal by performing amplitude modulation.

60. The sound enrichment system of claim 34, wherein the at least one signal modulator is configured to randomly adjust the noise signal at the rate that is slower than the rate of the amplitude variation in the noise signal by a factor of at least ten.

61. A method of providing a noise enriched sound signal for provision of relief of tinnitus, the method comprising: obtaining a noise signal, the noise signal comprising a white or color noise signal; obtaining an output from a detector; adjusting the noise signal to an adjusted noise signal based at least in part on the output from the detector, wherein the noise signal is adjusted randomly, and wherein a rate at which the noise signal is adjusted is slower than a rate of an amplitude variation in the noise signal; generating an acoustic signal based on the adjusted noise signal; and presenting the acoustic signal to a tinnitus-suffering person.

62. The method of claim 61, wherein the detector comprises a microphone.

63. The method of claim 61, wherein the noise signal is adjusted based on an analysis of the output from the detector.

64. The method of claim 61, wherein the output from the detector indicates a characteristic of an environment.

65. The method of claim 61, wherein the act of adjusting the noise signal comprises performing amplitude modulation.

66. The method of claim 61, wherein the noise signal is adjusted randomly at the rate that is slower than the rate of the amplitude variation in the noise signal by a factor of at least ten.

67. A sound enrichment system for provision of tinnitus relief, the sound enrichment system comprising:
a noise generator;
at least one signal modulator configured to perform modulation of a noise signal to obtain a modulated noise signal, the noise signal obtained using the noise generator, the noise signal comprising a white or color noise, wherein the modulation comprises at least two adjacent modulation peaks separated by a period that is longer than a period between two adjacent signal peaks in the noise signal; and
an output transducer for conversion of the modulated noise signal to obtain an acoustic signal for presentation to a user.

* * * * *